United States Patent
Boelsterli

(10) Patent No.: US 6,355,409 B1
(45) Date of Patent: Mar. 12, 2002

(54) TAGATOSE AS A CYTOPROTECTIVE SUPPLEMENT FOR THE REMOVAL AND/OR STORAGE OF ORGANS TO REDUCE REPERFUSION INJURY

(75) Inventor: Urs A. Boelsterli, Pfeffingen (CH)

(73) Assignee: Biospherics Incorporated, Beltsville, MD (US)

( * ) Notice: Subject to any disclaimer, the term of this patent is extended or adjusted under 35 U.S.C. 154(b) by 0 days.

(21) Appl. No.: 09/654,787

(22) Filed: Sep. 1, 2000

(51) Int. Cl.$^7$ ................................................. A01N 1/02
(52) U.S. Cl. ........................................................ 435/1.1
(58) Field of Search ........................................... 435/1.1

(56) References Cited

U.S. PATENT DOCUMENTS

| | | | |
|---|---|---|---|
| 5,356,879 A | 10/1994 | Zehner | 514/25 |
| 5,407,793 A * | 4/1995 | Del Nido et al. | 435/1 |

OTHER PUBLICATIONS

Brass et al., "Evaluation of University of Wisconsin cold-storage solution in wam hypoxic perfusion of rat liver: the addition of fructose reduces injury", Gastroenterology 105 (5) : 1455–63 (1993).*

Rognstad, "Gluconeogenesis from D–tagatose by isolated rat and hamster liver cells", FEBS Letters 52 (2) : 292–4 (1975).*

Drugas, G.T., Paidas, C.N., Yahanda, A.M., Ferguson, D., Clemens, M.G. Conjugated desferrioxamine attenuates hepatic microvascular injury following ischemica/reperfusion. Circ. *Shock* 34: 278–283 (1991).

Valeri, F., Boess, F., Wolf, A., Goldlin, C., and Boelsterli, U.A. Fructose and tagatose protect against oxidative cell injury by iron chelation, *Free Radic. Biol. Med.* 22: 257–268 (1997).

Paterna, J.C., Boess, F., Staubli, A., and Boelsterli, U.A. Antioxidant and cytoprotective properties of D–tagatose in cultured murine hepatocytes. *Toxicol. Appl. Pharmacol.* 148: 117–125 (1998).

Zeid, I.M., Bronk, S.F., Fesmier, P.J., and Gores, G. Cytoprotection by fructose and other ketohexoses during bile salt–induced apoptosis of hepatocytes. *Hepatology* 25: 81–86 (1997).

Charley, P.J., Sarkar, B., Stitt, C.F., Saltman, P. Chelation of iron by sugars. *Biochem. Biophys. Acta 69*: 313–321 (1963).

Davis, P.S., Deller, D.J., Prediction and demonstration of iron chelating ability of sugars. *Nature* 212: 404–405 (1966).

Tonkovic, M. New approach to the complexation of iron(III) with fructose. *Carbohydr. Res.* 254: 277–280 (1994).

Natori, S., Selzner, M., Valentino, K.L., Fritz, L.C., Srinivasan, A., Clavien, P.A., and Gores, G.J. Apoptosis of sinusoidal endothelial cells occurs during liver preservation injury by a caspase–dependent mechanism. *Transplatation 68:* 89–96 (1999).

Lemasters, J.J., and Thurman, R.G., Reperfusion Injury After Liver Preservation for Transplatation, *Annu. Rev. Pharmacol Toxicol 37* 327–38 (1997).

Jaeschke, H., and Farhood, A., Neutrophil—and Kupffer cell–induced oxidant stress and ischemia–reperfusion injury in rat liver. *Am. J. Physiol.* 260: G355–G362 (1991).

Bilzer, M., Paumgartner, G., and Gerbers, A.L. Glutathione protects the rat liver against reperfusion injury after hypothermic preservation. *Gatroenterology* 117:200–210 (1999).

Baker, C.J., Longoria, J., Gade, P.V., Starnes, V.A., Barr, M.L. Addition of a water–soluble alpha–tocopherol analogue to University of Wisconsin solution improves endothelial viability and decreases lung reperfusion injury. *J. Surg. Res.* 86: 145–149 (1999).

Buemann et al., "Effects of Oral–D–Tagatose, A Stereoisomer of D–Fructose, on Liver Metabolism in Man as Examined by P–Magnetic Resonance Spectroscopy", *Metabolism*, vol. 45, No. 10 (Oct.), 2000; pp. 1335–1339.

Donner et al., "D–tagatose, a novel hexose: acute effects on carbohydrate tolerance in subjects with an without type 2 diabetes", *Diabetes Obesity and Metabolism*, 1999;pp. 285–291.

Livesey et al., D–Tagatose Is a Bulk Sweetner with Zero Engergy Determined in Rats, 1996 American Institute Nutrition, pp. 1601–1609.

* cited by examiner

*Primary Examiner*—Sandra E. Saucier
(74) *Attorney, Agent, or Firm*—Robert H. Berdo; Garrett V. Davis

(57) ABSTRACT

Tagatose is added to an organ storage and preservative solution to reduce reperfusion injury of the organ during surgery and/or following removal of the organ from a subject.

8 Claims, No Drawings

TAGATOSE AS A CYTOPROTECTIVE SUPPLEMENT FOR THE REMOVAL AND/OR STORAGE OF ORGANS TO REDUCE REPERFUSION INJURY

BACKGROUND OF THE INVENTION

This invention relates to compositions for and methods of reducing and eliminating injuries to organs subjected to ischemic episodes.

Liver transplantation has become an important therapy for patients with end-stage liver disease. Reperfusion injury, however, remains a serious problem that limits the use of this method. Reperfusion injury is the major cause for graft rejection, retransplantation and even mortality. Liver damage is the consequence of ischemica during organ transplantation and is triggered by reestablishing blood flow through the vascular system of the organ. This results in the generation of reactive oxygen species (ROS) by nonparenchymal cells, the development of oxidative stress, and cell demise, mostly by apoptosis in the liver. The oxidative stress occurs initially in the vasculature (and not inside the hepatic parenchymal cells) and is produced by the resident macrophages (Kupffer cells) in the liver. Subsequently, during the following hours, neutrophils can infiltrate into the liver, accumulate, and in turn can produce a second wave of ROS.

Because oxidative stress in the principal cause of reperfusion injury, a number of antioxidant therapies have been introduced to minimize damage. For example, addition of superoxide dismutase to the perfusate to degrade superoxide anion radicals, inclusion of monoclonal antibodies directed against neutrophils to prevent PMN-induced damage, or supplementation of the perfusate with glutathione as an extracellular radical scavenger and antioxidant, have been successfully used in counteracting oxidative stress-induced endothlial cell injury.

In particular, the addition of deferoxamine to the perfusate has yielded beneficial effects on reperfusion injury. Deferoxamine is a clinically used iron chelator that prevents the redox cycling of iron and thus precludes the iron-catalyzed formation of injurious hydroxyl radicals from hydrogen peroxide. Attenuation of reperfusion injury with deferoxamine has also corroborated the assumption that ROS, and in particular metal-catalyzed production of hydroxyl radicals, play a crucial role in reperfusion injury.

Unfortunately, the clinical relevance of antioxidant supplementation is limited by side effects or low efficacy. For example, deferoxamine can become toxic at high concentrations. Therefore, it is an object of this invention to provide better antioxidant strategies to antagonize reperfusion injury in liver transplantation.

SUMMARY OF THE INVENTION

It has now been discovered that the addition of tagatose to an organ storage and preservative solution might reduce reperfusion injury of the organ during surgery and/or following removal of the organ from a subject. Tagatose exerts a dual effect that is beneficial in preserving the organ and preventing reperfusion injury. First, it is an aqueous-phase antioxidant. The putative mechanism of this protective effect against oxidative cell injury is iron chelation, sequestering iron from partitioning into membranes and promoting membrane lipid peroxidation. Second, exposure of organ cells such as liver cells to tagatose massively decreases ATP. The ATP- depleting effect is beneficial in preventing apoptosis, as ATP is required for the apoptotic process to be initiated.

DETAILED DESCRIPTION OF THE INVENTION

This invention permits the reduction of reperfusion injury in any organ, e.g., heart, kidney, intestines, liver, etc. The subject from which the organ is removed may be any mammalian species. The practice of this invention is especially useful in the transplantation of an organ from one human to another human.

The organ storage solution may include any commercial cold storage media such as Viaspan, also known as Belzer MPS, and UW (University of Wisconsin) solution.

Each L of Viaspan, which is a light yellow, sterile, non-pyrogenic solution for hypothermic flushing and storage of organs, contains: pentafraction (hydroxyethyl starch) 50 g, lactobionic acid 35.83 g, potassium phosphate monobasic 3.4 g, magnesium sulfate heptahydrate 1.23 g, raffinose pentahydrate 17.83 g, adenosine 1.34 g, allopurinol 0.136 g, total glutathione 0.922 g, potassium hydroxide q.s., sodium hydroxide adjusted to pH 7.4, water for injection q.s. The solution has an approximate calculated osmolarity of 320 mOsM, a sodium concentration of 29 mEq/L, a potassium concentration of 125 mEq/L, and a pH of approximately 7.4 at room temperature.

Preferably, the tagatose is D-tagatose and is added in an amount of from about 0.018 to about 0.36% by weight, based on the weight of the organ storage solution.

The following Examples illustrate the invention:

EXAMPLE 1

Use Of Tagatose In Removal And Storage Of Organ From A Donor

After the organ, e.g., a liver is accessed by surgery on a human subject, three liters of chilled tagatose solution containing about 0.36% by weight of tagatose are used to flush the blood from it and to cool the organ while still on the body. The tagatose solution contains the amounts of nutrients and electrolytes common to present day storage solutions, such as Viaspan. These added ingredients, necessary to maintain viability of the organ, are readily dissolved in the tagatose solution and do not react with the tagatose. The organ is then removed and placed into a chilled sterile container, holding more of the tagatose solution, for refrigerated storage until the transplant occurs.

EXAMPLE 2

Use Of Tagatose In Immediate Transplant Of Organ From Donor To Recipient

The ischemia time is shorter in this procedure than in Example 1. The donor organ is removed and perfused with tagatose solution containing about 0.36% by weight of tagatose that, again, contains the requisite nutrients and electrolytes. The organ is then placed into a sterile container that contains more of the same tagatose solution. That sterile container is placed into two more sterile containers and is then placed on ice for immediate transit to the organ recipient.

EXAMPLE 3

Use Of Tagatose In Organ Preservation With Lengthy Cold Ischemia Time.

The organ is removed as described in Example 1. It is flushed and perfused with tagatose solution, containing about 0.36% by weight of tagatose, and containing the requisite nutrients and electrolytes. The organ is placed in a sterile container with more of the same tagatose solution. Two protocols may be used for storage a. The organ is placed into a sterile container, such as a zip lock bag, containing the tagatose solution described above. The bag is then successively placed into two more sterile containers before being placed in a container on ice, or b. The organ is placed on a pulsatile pump that continually perfuses the organ with chilled tagatose solution, as described above. While requiring additional tagatose solution, this procedure replaces the need for cold storage of the organ on ice by allowing the tagatose solution fluid to cool down the organ.

In each of the above Examples, it is found that the addition of tagatose to the organ storage solution reduces reperfusion injury of the organ.

I claim:

1. A method for reducing reperfusion injury of an organ during surgery and/or following removal of the organ from a subject which comprises placing the organ in an organ storage and preservative solution, said solution containing tagatose.

2. The method of claim 1 wherein said organ storage and preservative solution is a solution containing per liter pentafraction (hydroxyethyl starch) 50 g, lactobionic acid 35.83 g, potassium phosphate monobasic 3.4 g, magnesium sulfate heptahydrate 1.23 g, raffinose pentahydrate 17.83 g, adenosine 1.34 g, allopurinol 0.136 g, total glutathione 0.922 g, potassium hydroxide q.s., sodium hydroxide adjust to pH 7.4, water for injection q.s., said solution containing tagatose.

3. The method of claim 2 wherein said organ is a liver.

4. The method of claim 2 wherein said organ is a kidney.

5. The method of claim 2 wherein said organ is a heart.

6. The method of claim 2 wherein said organ is an intestine.

7. The method of claim 2 wherein said tagatose comprises from about 0.018 to 0.36 percent by weight of the organ storage and preservative solution.

8. The method of claim 2 wherein said subject is a human.

\* \* \* \* \*